(12) United States Patent
Dravida

(10) Patent No.: US 10,022,402 B2
(45) Date of Patent: Jul. 17, 2018

(54) ALLOGENIC MESENDRITIC VECTOR FOR OVARIAN CANCER

(71) Applicant: Subhadra Dravida, Telangana (IN)

(72) Inventor: Subhadra Dravida, Telangana (IN)

(73) Assignee: Subhadra Dravida, Hyderabad (IN)

(*) Notice: Subject to any disclaimer, the term of this patent is extended or adjusted under 35 U.S.C. 154(b) by 182 days.

(21) Appl. No.: 14/649,212

(22) PCT Filed: Dec. 2, 2013

(86) PCT No.: PCT/IB2013/002684
§ 371 (c)(1),
(2) Date: Jun. 3, 2015

(87) PCT Pub. No.: WO2014/087217
PCT Pub. Date: Jun. 12, 2014

(65) Prior Publication Data
US 2015/0306145 A1    Oct. 29, 2015

(30) Foreign Application Priority Data

Dec. 3, 2012  (IN) .......................... 5030/CHE/2012

(51) Int. Cl.
| | | |
|---|---|---|
| *A61K 35/28* | (2015.01) | |
| *A61K 35/15* | (2015.01) | |
| *C12N 5/0784* | (2010.01) | |
| *C12N 5/0775* | (2010.01) | |

(52) U.S. Cl.
CPC .............. *A61K 35/28* (2013.01); *A61K 35/15* (2013.01); *C12N 5/0639* (2013.01); *C12N 5/0665* (2013.01); *C12N 2502/30* (2013.01)

(58) Field of Classification Search
CPC .......... A61K 39/39558; A61K 2300/00; A61K 31/675; A61K 35/28; A61K 35/15; A61K 38/00; A61K 45/06; A61K 2039/505; A61K 2039/507; A61K 2039/5152; A61K 38/1774; A61K 39/0011; A61K 39/3955; A61K 2039/5154; A61K 31/343; A61K 31/57; A61K 47/34; A61K 47/44; A61K 9/0019; A61K 35/17; A61K 2035/124; A61K 35/50; A61K 2035/122; A61K 31/56; A61K 31/565; A61K 35/39; A61K 31/454; A61K 31/568; C12N 2502/30; C12N 5/0639; C12N 5/0665
See application file for complete search history.

(56) References Cited

U.S. PATENT DOCUMENTS

| | | |
|---|---|---|
| 6,194,152 B1 | 2/2001 | Laus et al. |
| 6,210,662 B1 | 4/2001 | Laus et al. |
| 7,414,108 B2 | 8/2008 | Laus et al. |
| 2010/0055076 A1 | 3/2010 | Lim et al. |

FOREIGN PATENT DOCUMENTS

| | | |
|---|---|---|
| KR | 20080078204 | 8/2008 |
| WO | WO2008102937 | 8/2008 |

OTHER PUBLICATIONS

Gong J et al, Fusions of . . . Induce Antitumor Immunity, The Journal of Immunology, Aug. 1, 2000, pp. 1705-1711, vol. 165, No. 3, The Americal Association of Immunology, US.
I Hus et al, Allogenic dendritic cells pulsed with tumor lysates . . . early-stage B-cell chronic lymphocytic leukemia, Leukemia, Jun. 30, 2005, pp. 1621-1627, vol. 19, No. 9.
Ralf Hass et al, Mesenchymal stem cells as . . . microenvironment, Cell Communication and Signalling, Sep. 3, 2012, p. 26, Vool. 10, No. 1, Biomed Central, London, GB.
S Chiesa et al, Mesenchymal stem cells impair in vivo . . . dendritic cells, Proceedings of the National Academic Sciences, Sep. 29, 2011, pp. 173, vol. 108, No. 42.
English K et al, Murine mesenchymal stem cells supress . . . maturation and antigen presentation, Immunology Letters, Jan. 15, 2008, vol. 115, No. 1, Elsevier BV, NL.
B. Zhang et al, Mesenchymal stem cells induce mature . . . regulatory dendritic cell population, Blood, Oct. 2, 2008, pp. 46-57, vol. 113, No. 1.

*Primary Examiner* — Debbie K Ware

(57) ABSTRACT

A method of preparing an allogenic dendritic stem cell vaccine for treating ovarian cancers is disclosed. The method comprises, (a) collecting blood sample from an allogenic donor in a sterile collection bag, (b) separating viable mesenchymal stem cells inoculums by centrifuging the blood sample, suspending said mesenchymal stem cells inoculum in proliferation medium, plating the cells in a flask and incubated, and collecting cells adherent to the flask and further harvesting and expanding said adherent cells, (c) preparing myeloid dendritic cells by isolating, harvesting and culturing said blood sample source using myeloid dendritic isolation kit, (d) mixing the adherent cells obtained. Finally, (e) the composition of the adherent cells obtained in step (d) to the myeloid dendritic cells obtained in step (c) at a ratio of 90:10 and printing the cellular vectors with patient tumor derived heterogeneous progenitors.

3 Claims, 4 Drawing Sheets

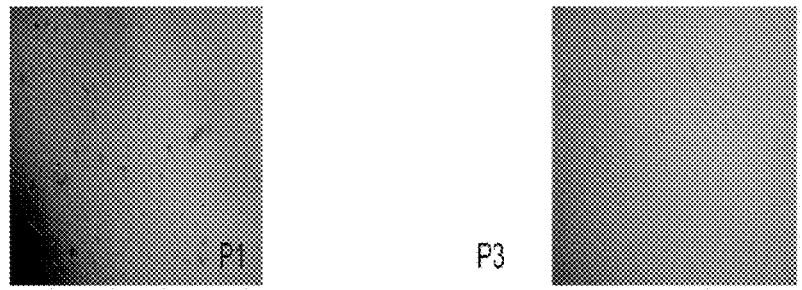
Figure 3
| Sample Cord blood | CD 34 | CD90 % expression | CD105 % expression | HLA-ABC % expression |
|---|---|---|---|---|
| Cultured MSCs @ P0 | - Ve | 70-78 | 83-90 | 40-53 |
| Cultured MSCs @ P3 | - Ve | 73-85 | 87-90 | 45-50 |
Figure 4
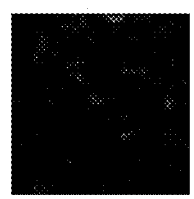
Figure 5

ALLOGENIC MESENDRITIC VECTOR FOR OVARIAN CANCER

FIELD OF THE INVENTION

The present invention relates to the technology of progenitor and immune privileged cells and its clinical application in filing a solution for ovarian cancers, more particularly belongs to the method of preparing a novel pharmacocellular composition comprising mesenchymal and dendritic cells as cellular vectors in treating ovarian cancers.

BACKGROUND AND PRIOR ART

Ovarian cancer is a type of solid tumour that begins in the ovaries. Ovarian cancer symptoms are mistaken for more-common conditions and so with late diagnosis, cure is not possible. The treatment of ovarian cancer is based on the stage of the disease which is a reflection of the extent or spread of the cancer to other parts of the body. The stages of cancer are explained as below:

Stage I: If the cancer is confined to one or both ovaries.

Stage II: If either one or both of the ovaries are involved and the tumour has spread to the uterus and/or the fallopian tubes or other sites in the pelvis.

Stage III: If one or both of the ovaries are involved and the tumour has spread to lymph nodes or other sites such as outside the pelvis region but is still within the abdominal cavity, such as the surface of the intestine or liver.

Stage IV: If one or both ovaries are involved and the tumour has spread outside the abdomen or has spread to the inside of the liver.

Autologous Dendritic Cell Potency to activate the naïve T– cells of Immune system to treat tumour related malignant diseases is a revolutionary medical treatment approach Immune system has the potential to eliminate neoplastic cells. Escape from immune surveillance is believed to be a fundamental biological feature of malignant disease in man, which contributes to uncontrolled tumour growth, eventually leading to death of the host. Defects in immune response in patients with a variety of tumours and in tumour-bearing animals have been well documented. The key element is the induction of the anti-cancer immune response, namely Tumor Associated Antigens (TAAg) presentation to T cells in a tumour-bearing host (human and animal). Bone marrow-derived Antigen Presenting Cells (APCs) were shown to play an important role in the presentation of TAAgs, a function previously assigned predominantly to tumour cells. Therefore, elucidation of the role of such APCs, in particular Dendritic Cells (DCs) helped to better understand the mechanisms underlying anti-tumour immune responses and, improve the effectiveness of anti-cancer immunity in tumour-bearing hosts.

Dendritic cells are Antigen Presenting Cells (APCs) which play a critical role in the regulation of the adaptive immune response. Dendritic cells (DCs) are unique and have been referred to as "professional" APCs. The principal function of DCs is to present antigens; only DCs have the ability to induce a primary immune response in resting naïve T lymphocytes. To perform this function, DCs capture antigens, process them, and present them on the cell surface along with appropriate co-stimulatory molecules. DCs also play a role in the maintenance of B cell function and recall responses. Thus, DCs are critical in the establishment of immunological memory. The unique ability of DCs to activate naïve and memory CD4+ and CD8+ T cells suggests that they could be used for the induction of a specific antitumour immunity. In the past few years, several in vitro and in vivo studies in rodents and humans have demonstrated that immunizations with DCs pulsed with tumour antigens resulted in protective immunity and rejection of established tumours in various malignancies.

Ovarian cancer precursors, originating from the bone marrow, migrate to virtually every organ in the body, where immature DCs take up the surrounding antigens. After antigen uptake, the DCs mature, co-stimulatory molecules (e.g., CD40, CD80, CD86) are up regulated and the DCs migrate to the lymphoid tissues where they activate effector T cells. Consequently, tumour antigen-loaded DCs may be ideal cells for the generation and amplification of antitumour responses in a vaccination setting. Several clinical studies have shown distinct clinical responses after vaccination with tumour antigen-loaded, autologous DCs. Despite these successes, the only problem remaining is limited number of DCs available for immunotherapy. As DCs are not only important for the initiation of specific cytotoxic T cell (CTL) responses, but also for the maintenance of protective CTL, it may be crucial to repeatedly vaccinate cancer patients with tumor antigen-loaded DCs. Studies reported that myeloid dendritic cells (mDCs) derived in vitro suppressed angiogenesis in vivo through production of interleukin 12, implicating the role of mDCs in tumour pathology. The therapeutic implications of recent findings state that specific myeloid cell populations of dendritic cells modulate the responses of tumours to agents such as chemotherapy and some anti-angiogenic therapies.

Mesenchymal stem cells (MSCs) targeted to cancers are expected to contribute many soluble factors such as mitogens, extracellular matrix proteins, angiogenic and inflammatory factors, as well as exosomes with as yet poorly defined potentials, once resident in the Tumour Micro Environment (TME). MSCs are also expected to affect tumour-associated leukocytes either directly by cell-cell contact or indirectly by the secretion of trophic factors. MSCs are known to affect the proliferation and differentiation of dendritic cells, monocytes/macrophages, B and T cells, NK cells, and even mast cells. There has been a great deal of debate in the field in trying to assert the role of MSCs in anti-tumour mechanisms.

Ovarian cancer treatment usually involves surgery, chemotherapy and autologous dendritic cell therapy. The primary one is surgery at which time the cancer is removed from the ovary and from as many other sites as is possible. Chemotherapy is the second important modality which uses drugs to kill the cancer cells. The other modality is radiation treatment, which is used in only certain instances. It utilizes high energy x-rays to kill cancer cells. Second look surgery and Salvage chemotherapy are the other treatment options to address recurrent types of ovarian cancers. High-dose chemotherapy accompanied with Autologous Bone Marrow Transplantation (ABMT) and Peripheral Blood Stem Cell transplantation (PBSCT) produces high response rates (70-82%) in patients with resistance to primary chemotherapy, but the responses are generally of limited duration. Such approaches are generally limited to clinical trials, and are also being tested for first line therapy. Autologous dendritic cell therapy is being practiced as experimental personalized therapy addressing relapsed/refractory types. This service involves the patient's own immune system to kill the cancer cells. These immune cells are called dendritic cells that are monocytes and are harvested from patient's blood. The dendritic cells are cultured in a special classified laboratory, formulated into a vaccine using the patient's own tumour cells.

U.S. Pat. No. 7,414,108 entitled "Composition and method for producing an immune response against tumour-related antigens" discloses a novel composition and a method for producing an immune response that is directed against a tumour-related antigen. This invention uses mouse prostatic acid phosphatase (mPAP) which can be used as a xenogeneic antigen to induce prostate-directed immunity in other mammalian species. The vehicles that are used for this induction include viruses such as vaccinia virus or dendritic cells which express mPAP, human PAP or rat PAP.

U.S. Pat. No. 6,210,662 entitled "Immunostimulatory composition" discloses an invention which is directed to a therapeutic composition for stimulating a cellular immune response. The novel composition disclosed is an isolated, stimulated potent antigen presenting cell such as activated dendritic cell that can activate T-cells to produce a multivalent cellular immune response against a selected antigen. The potent antigen presenting cells are stimulated by exposing them in vitro to a polypeptide complex which is essentially of a dendritic cell-binding protein and a polypeptide antigen.

U.S. Pat. No. 6,194,152 entitled "Prostate tumour polynucleotide compositions and methods of detection thereof" provides chimeric polypeptide molecules comprising the polypeptides fused to heterologous polypeptide sequences, and antibodies which bind to the polypeptides. It also provides a method for producing the polypeptides disclosed above, as are detection assays that detect the presence of tumour cells in tissue or bodily fluid samples and a method for identifying novel compositions which modulate the activity of prostate tumour antigens and the use of such compositions in diagnosis and treatment of disease.

US Patent Application 20100055076 entitled "Mesenchymal stem cell-mediated autologous dendritic cells with increased immune suppression" describes a pharmaceutical composition comprising the dendritic cells capable of inducing immunosuppressive responses that has an enhanced potential to suppress immune responses can be utilized for treating various diseases.

The composition as disclosed in the present invention was prepared/adopted in treating the tumour has always been for autologous applications with autologous preparations and compositions. The dendritic cells were postulated to target the tumours with loaded antigens and there are not many global groups working on dendritic cell vaccines which adopt the properties of mesenchymal stem cells for ovarian cancer treatment. Allogenic dendritic cells—mesenchymal stem cells combination (Mesendritic) as the vector in targeted ovarian cancer treatment is innovative concept in cancer therapeutics.

SUMMARY

A novel composition administered as vector in treating ovarian cancer comprising dendritic special type and mesenchymal stem cells harvested in allogenic donated cord blood source that are primed with patient's tumour antigens. The present invention also discloses a method for preparing a novel composition as specified above. The novelty of the invention resides in the mixture used which is human cord blood derived allogenic mesenchymal stem cells and allogenic dendritic cells. Both the cell types in the presence of each other would affect the surface marker profiles on each type to benefit the composition to neutralize the unwanted immune-stimulation post allogenic infusion while targeting tumour zone with no immune suppression prescribed in the treatment. The technology exploits the properties of mesenchymal stem cells and dendritic cells in killing the targeted tumour cells benefiting the patient with no further morbidity of either bone marrow or peripheral blood aspirations for obtaining higher yields of either therapeutic dendritic cells or mesenchymal stem cells.

BRIEF DESCRIPTION OF THE DRAWINGS

For a more complete understanding of example embodiments of the present technology, reference is now made to the following descriptions taken in connection with the accompanying drawings in which:

FIG. 3 shows the cultured mesenchymal stem cells at Passage 1 (P1) and Passage 3 (P3);

FIG. 4 shows a table illustrating the comparative expressions of surface markers on mesenchymal stem cells at Passage 0 (P0) and Passage (P3) harvested and expanded from the cord blood source (Thali$^R$—Image based cytometer data);

FIG. 5 shows cultured mesenchymal stem cells at P3 showing cytoplasmic staining of TIMP-1;

DETAILED DESCRIPTION OF THE PREFERRED EMBODIMENTS

Figure 1:
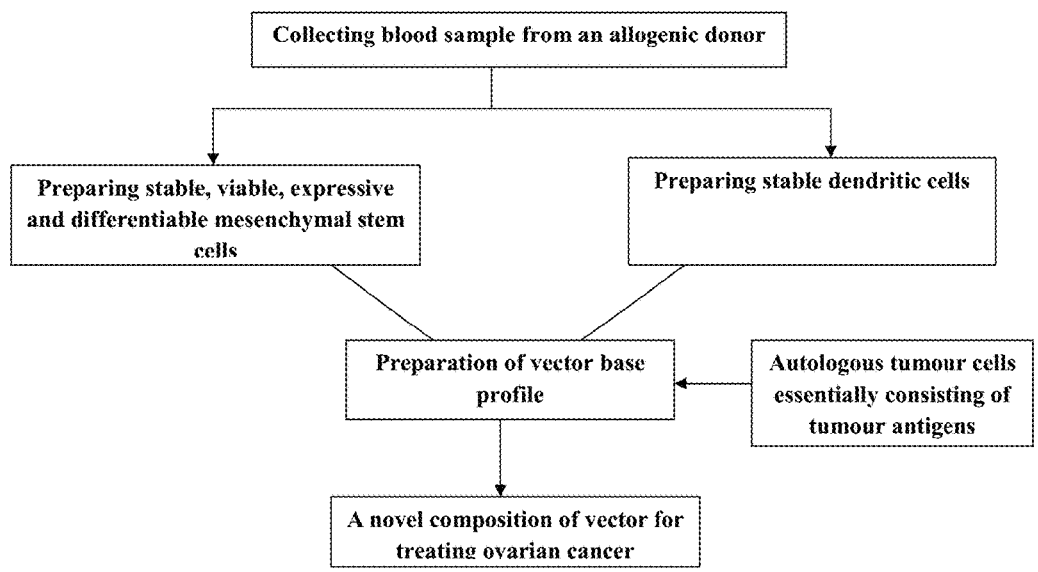
FIG. 1 shows a flowchart illustrating the method of preparation of the vector composition.

In the following description, for purposes of explanation, numerous specific details are set forth in order to provide a thorough understanding of the present technology. It will be apparent, however, to the one skilled in the art that the present technology can be practiced without these specific details.

Reference in this specification to "one embodiment" or "an embodiment" means that a particular feature, structure, or characteristic described in connection with the embodiment is included in at least one embodiment of the present technology. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be required for some embodiments but not other embodiments.

Moreover, although the following description contains many specifics for the purposes of illustration, anyone skilled in the art will appreciate that many variations and/or alterations to said details are within the scope of the present technology. Similarly, although many of the features of the present technology are described in terms of each other, or in conjunction with each other, one skilled in the art will appreciate that many of these features can be provided independently of other features. Accordingly, this description of the present technology is set forth without any loss of generality to, and without imposing limitations upon, the present technology.

The present invention discloses a new approach of allogenic dendritic-stem cell vaccine platform to treat all kinds of ovarian cancers. The treatment technology proposed is a combination of adult immune privileged mesenchymal stem cells and antigen presenting dendritic cells especially myeloid dendritic cells as the cellular vectors primed to targeted killing of tumour cells. The unique source of cellular derivatives i.e. human umbilical cord blood is one of it's kind and is shown to reside naive and unmanipulated cellular population with therapeutic values attributed.

The abundant allogenic donated cord blood source is used to harvest both dendritic special type and mesenchymal stem cells equilibrated package primed with patient's tumour antigens for a targeted treatment regime. The individual roles of dendritic cells and mesenchymal stem cells in immunomodulation is exploited in developing this new combinatorial platform of cellular vectors for targeted killing of tumour cells in the patient's body. The source proposed here in developing the technology is a biological discard and is available in profusion for proposed clinical application. The main advantage of this composition to treat ovarian cancers will not subject the suffering patients for any longer waiting for dendritic cells to be cultured as in for autologous preparations and also for a culture independent yield used as cellular formulation for clinical applications.

The process of the immune privileged Mesendritic therapeutic vector and the clinical application modality are proprietary in nature of the technology proposed.

The present invention describes a novel composition that can used as vaccines for treating ovarian cancer comprising mesenchymal stem cells and antigen presenting myeloid dendritic cells obtained from an allogenic source of cord blood primed with antigens obtained from autologous tumour cells and a method of preparing vaccines that includes allogenic mesenchymal stem cells and dendritic cells primed with antigens obtained from the autologous tumour cells as referred in FIG. 1.

Figure 2:
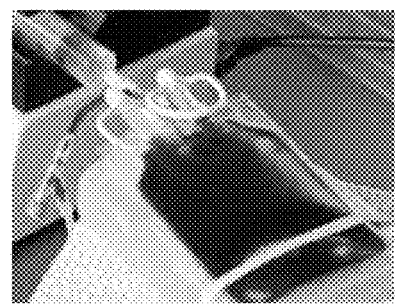
FIG. 2 shows the collected cord blood stored in a sterile collection bag.

In the present invention, both the mesenchymal stem cells and antigen presenting dendritic cells are isolated from the allogenic blood source. In one of the embodiment of the invention, the Umbilical Cord Blood samples are collected from full-term delivery cases with previous consent from the mothers according to the Institute's ethical and scientific committee guidelines. FIG. 2 shows the collected cord blood stored in a sterile collection bag.

Preparation of Mesenchymal Stem Cells:

50 ml aliquots of the collected cord blood from the bag is aspirated out in sterile 50 ml syringes to centrifuge using percoll gradient separation method for buffy coat containing mononuclear cells (MNCs) separation. The 3 ml of buffy coat obtained after centrifugation was suspended in proliferation medium consisting of DMEM-F12 (Gibo, Life Technologies, Carlsbad, Calif., USA) with 20% FBS (GIBCO, USA), 20 ng/ml fibroblast growth factor (FGF)-2 (Chemicon, Millipore, Billerica, Mass., USA), 1% penicillin/streptomycin (Gibco) and was plated in T25 flasks at a density of $5 \times 10^6$ cells/ml.

After 24 hours of incubation at 37° C. with 5% $CO_2$, the non-adherent cells were washed off and the cells that were attached to the flask were cultured further with medium being replenished every alternate day. The adherent fibroblastic cell type once confluent in the flask (Passage 0, P0) is trypsinized to next passages for expansion of the cells, thrice (Passage 3, P3). FIG. 3 shows the cultured mesenchymal stem cells at Passage 1 (P1) and Passage 3 (P3). The adherent cells obtained at P0 and P3 harvested and expanded from the cord blood source are analyzed for the expressions of surface markers namely CD34, CD90, CD105, HLA-ABC with image cell cytometry (Thali$^R$, Invitrogen, USA).

FIG. 4 shows a table illustrating the comparative expressions of surface markers on mesenchymal stem cells at P0 and P3 harvested and expanded from the cord blood source (Thali$^R$—Image based cytometer data). With reference to the FIG. 4, mesenchymal stem cells at P0 and P3 are found to show variation in the surface marker expression percentages although no significance is attributed to any factor. Therefore, P0 and P3 mesenchymal stem cells are two different cell populations in terms of the composition expressing varied surface markers and the cell cycle state.

Mesenchymal stem cells at P0 and P3 (70-80% confluent as shown in FIG. 3) are stained with anti-TIMP-1 antibody (Abcam; 1:200); FITC conjugated secondary antibody. Immunofluorescence of the cells as observed, shows more than 15% of the number of cells test positive for TIMP-1 expression at P0 compared to P3 cells as shown in FIG. 5 which shows cultured mesenchymal stem cells at P3 showing cytoplasmic staining of TIMP-1. The positively stained green cells are counted per focus of 100 cells and an average of five foci is compared between P0 and P3 cultures.

Figure 6:
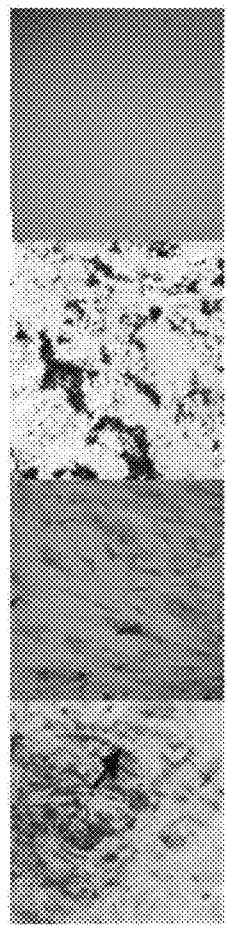
FIG. 6 shows the results of P0 mesenchymal stem cells trans-differentiated in-vitro wherein 6A shows the phase contrast mesenchymal stem cells micrograph (10×); 6B shows Von Kossa stained calcium deposits in mesenchymal stem cells differentiated to osteocytes culture; 6C shows Oil-O-Red stained adipocytes; and 6D shows Alcian blue stained chondrocytic cellular cluster.

Trans-differentiation of the P0 and P3 mesenchymal stem cells in-vitro showed that both the cultures are equally able to become osteocytes, chondrocytes and adipocytes with positive staining for vonkossa, alcain blue and oil-o-red chemicals. FIG. 6 shows the results of P0 mesenchymal stem cells trans-differentiated in-vitro wherein 6A shows the phase contrast mesenchymal stem cells—micrograph (10×); 6B shows Von Kossa stained calcium deposits in the mesenchymal stem cells differentiated to osteocytes culture; 6C shows Oil-O-Red stained adipocytes; and 6D shows Alcian blue stained chondrocytic cellular cultures.

Figure 7:
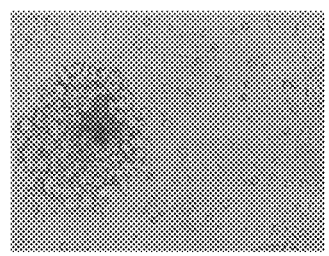
FIG. 7 shows the micrograph (10×) of MACS segregated and seeded dendritic cells from cord blood.

Preparation of Antigen Presenting Dendritic Cells:

Dendritic Cells suitable for administration to subjects can be isolated or obtained from the allogenic cord blood source by culturing and harvesting using standard techniques known in the prior art. $2 \times 10^9$ cells (adjusted with Normal Saline, 10 ml), of Cord blood collected in the bag is prepared for mDCs isolation using myeloid dendritic cell isolation kit (MACS Miltenyi Biotech, Germany). FIG. 7 shows the micrograph (10×) of MACS segregated and seeded dendritic cells from cord blood.

Preparation of Cell Based Vector:

Mesenchymal stem cells at P0 and P3 are mixed in different pre-determined ratios with the myeloid dendritic cells (cell density ratios). Table 1 shows the different compositions of the vector cell base that can be prepared and named accordingly.

TABLE 1

| MSCs ratio | mDCs ratio | Tube Code given |
|---|---|---|
| 1 (P0 + P1) (50:50) | 1 | MD1 |
| 2 (P0 + P1) (50:50) | 1 | MD2 |

TABLE 1-continued

| MSCs ratio | mDCs ratio | Tube Code given |
|---|---|---|
| 3 (P0 + P1) (50:50) | 1 | MD3 |
| 4 (P0 + P1) (50:50) | 1 | MD4 |

Example 1

Figure 8A:
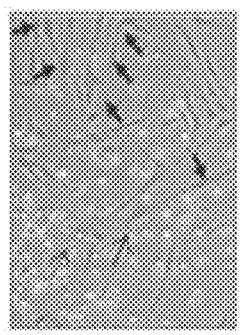
FIG. 8A shows the micrograph (10×) of the mixture of mesenchymal stem cells and dendritic cells at 1:1 ratio.
Figure 8B:
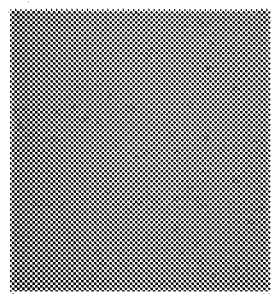
FIG. 8B shows 98% viability of the same mixture stained with Propidium Iodide.
Figure 8C:
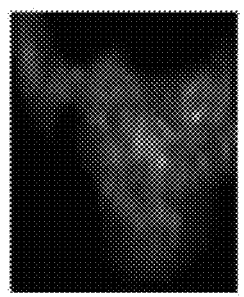
FIG. 8C is a representative photograph of 22% of cells testing positive for cytoplasmic stained green color with FITC conjugated secondary antibody against TIMP-1 antibody.

MD1 mixture is enumerated under the microscope and stained with Propidium Iodide (PI) to assess the viability. More than 98% of the cell mixture is recorded to be viable with only 2% of the cells stained red with PI. The cell mixture (1 ml) is seeded in growth medium containing DMEM-F12 and 10% FBS for overnight in a coated tissue culture plate. After 16 hours of sedimentation of the cells in the plate, the cells are fixed in paraformaldehyde (4%) and stained with anti-human TIMP-1 antibody. The Immunofluorescence of the cells showed 20-22% more cells test positive for cytoplasmic stained green color with FITC conjugated secondary antibody. FIG. 8A shows the photograph of the mesenchymal stem cells and dendritic cells mixture at 1:1 ratio; FIG. 8B shows 98% viability of the same mixture stained with Propidium Iodide; and FIG. 8C shows the photograph of 22% of cells, testing positive for cytoplasmic stained green color with FITC conjugated secondary antibody against TIMP-1 primary antibody.

Preparation of Vector and its Composition:

The biopsy (1-2 inches) of the tumor tissue obtained is macerated in a sterile container and the cell suspension in cell proliferation medium. 50-100 cells of the biopsy counted under the microscope is mixed with the vector cell based ratios as shown in Table 2.

TABLE 2

| MSCs ratio | mDCs ratio | Tumor cell number (autologous) |
|---|---|---|
| 1 (P0 + P1) (50:50) | 1 | 50-100 |
| 2 (P0 + P1) (50:50) | 1 | 50-100 |
| 3 (P0 + P1) (50:50) | 1 | 50-100 |
| 4 (P0 + P1) (50:50) | 1 | 50-100 |

Example 2

Tumor cell line ATCC IGROV1 cultured in RPMI 1640 supplemented with 10% Fetal Bovine Serum is sub cultured for 7 days. Cells are trypsinized and washed with the growth medium. Upto 200 cells counted in the growth medium is mixed with MD1 tube cells at room temperature. The stability of the vector prepared is checked for every one hour till 10 hrs of incubation at 37° C. with 5% $CO_2$ by evaluating the apoptosis. Till $10^{th}$ hour of the incubation, there was no abnormal apoptosis observed by Image cytometer using annexin V marker in the preparation establishing the stability of the mixture of cells in the presence of each other presenting as cell based vector candidacy for allogenic infusion targeting the solid tumor tissue.

REFERENCES

1. Yap T A, Carden C P, Kaye S B. Beyond chemotherapy: targeted therapies in ovarian cancer. Nature Rev Cancer 2009; 9:167-81. [PubMed: 19238149]
2. Jemal A, Siegel R, Ward E, et al. Cancer statistics, 2008. CA Cancer J Clin 2008; 58:71-96. [PubMed: 18287387]
3. Santin A D, Hermonat P L, Ravaggi A, et al. Induction of tumour-specific HLA class I-restricted CD8+ cytotoxic T lymphocytes by ovarian tumour antigen-pulsed autologous dendritic cells in patients with advanced ovarian cancer. Am J Obstet Gynecol 2000; 183:601-9. [PubMed: 10992180]
4. Santin A D, Bellone S, Ravaggi A, et al. Induction of ovarian tumour-specific CD8+ cytotoxic T lymphocytes by acid-eluted peptide-pulsed autologous dendritic cells. Obstet Gynecol 2000; 96:422-30. [PubMed: 10960637]
5. Zhao X, Wei Y Q, Peng Z L. Induction of T cell responses against autologous ovarian tumours with whole tumour cell lysate-pulsed dendritic cells. Immunol Invest 2001; 30:33-45. [PubMed: 11419910]
6. Gong J, Nikrui N, Chen D, et al. Fusions of human ovarian carcinoma cells with autologous or allogeneic dendritic cells induce anti-tumour immunity. J Immunol 2000; 165:1705-11. [PubMed: 10903782]
7. Chiang C L L, Ledermann J A, Rad A N, et al. Hypochlorous acid enhances immunogenicity and uptake of allogeneic ovarian tumour cells by dendritic cells to cross-prime tumour-specific T cells. Cancer Immunol Immunother 2006; 55: 1384-95. [PubMed: 16463039]
8. Hernando J J, Park T W, Kubler K, et al. Vaccination with autologous tumour antigen-pulsed dendritic cells in advanced gynaecological malignancies: clinical and immunological evaluation of a phase I trial. Cancer Immunol Immunother 2002; 51:45-52. [PubMed: 11845259]
9. Cannon M J, Santin A D, O'Brien T J. Immunological treatment of ovarian cancer. Curr Opin Obstet Gynecol 2004; 16:87-92. [PubMed: 15128013]
10. Aggarwal, S. & Pittenger, M. F. (2005). Human mesenchymal stem cells modulate allogeneic immune cell responses. *Blood*, Vol. 105, pp 1815-1822, ISSN 0006-4971, doi: 10.1182/blood-2004-04-1559
11. Barleon, B. et al. (1996). Migration of human monocytes in response to vascular endothelial growth factor (VEGF) is mediated via the VEGF receptor flt-1. *Blood*, Vol. 87, pp 3336-3343, ISSN 0006-4971
12. Bian, Z-Y. et al. (2010). Human mesenchymal stem cells promote growth of osteosarcoma: Involvement of interleukin-6 in the interaction between human mesenchymal stem cells and Saos-2. *Cancer Sci.*, Vol. 101, pp 2554-2560, doi: 10.1111/j.1349-7006.2010.01731.x
13. Bisping, G. et al. (2009). Bortezomib, dexamethasone, and fibroblast growth factor receptor 3-specific tyrosine kinase inhibitor in t(4;14) myeloma. *Clin. Cancer Res.*, Vol. 15, pp 520-531, doi: 10.1158/1078-0432.CCR-08-1612.
14. www.clinicaltrials.gov

What is claimed is:

1. A method of preparation of an allogenic dendritic stem cell vaccine for treating ovarian cancers including allogenic blood source derived mesenchymal stem cells and antigen presenting myeloid dendritic cells, comprising the steps of:
   a. collecting blood sample from an allogenic donor in a sterile collection bag;
   b. separating viable, mesenchymal stem cells inoculums by centrifuging 50 ml aliquots of the said blood sample using percoll gradient separation method for buffy coat containing mononuclear cells for separation; suspending 3 ml of the said mesenchymal stem cells inoculums in proliferation medium, plating enumerated round cells in a T25 flask at a density of: $5 \times 10^6$ cells/ml and incubating at 37° C. with 5% $CO_2$ for 24 hours, collecting cells adherent to the flask and further culturing and expanding the said adherent cells with a progenitor selection medium being replenished every alternate day at passage P0; trypsinizing the said adherent cells positive for mesenchymal stem cell markers to subsequent passages of expansion thrice to obtain cells at passages P1, P2 and P3; harvesting and expanding the said adherent cells obtained from the passages P0 and P3 of expansion;

c. preparing myeloid dendritic cells by isolating, harvesting and culturing the said blood sample using myeloid dendritic isolation kit;

d. mixing the adherent cells obtained at passage P0 and P3 of expansion at a ratio of 50:50; and e. a composition of the adherent cells obtained in step (d) to the myeloid dendritic cells obtained in step (c) at a ratio of 90:10 and priming the cellular vectors (d+e) with patient tumor derived heterogeneous progenitors.

2. The method of claim 1 wherein the said blood sample is collected from a donated umbilical cord from a full-term delivery case with an informed prior consent.

3. A composition of an allogenic dendritic stem cell vaccine for treating ovarian cancers comprising allogenic blood source derived mesenchymal stem cells and antigen presenting myeloid dendritic cells at a ratio of 90:10, together primed with patient tumor derived heterogeneous progenitors, and a pharmaceutically acceptable carrier.

* * * * *